United States Patent
Hyppölä

[11] Patent Number: 5,857,457
[45] Date of Patent: Jan. 12, 1999

[54] POWDER INHALER WITH REMNANT MOVER AND CHAMBER

[75] Inventor: Jukka Hyppölä, Espoo, Finland

[73] Assignee: Orion-Yhtyma Oy, Espoo, Finland

[21] Appl. No.: 737,361

[22] PCT Filed: May 10, 1995

[86] PCT No.: PCT/FI95/00247

§ 371 Date: Nov. 8, 1996

§ 102(e) Date: Nov. 8, 1996

[87] PCT Pub. No.: WO95/31237

PCT Pub. Date: Nov. 23, 1995

[30] Foreign Application Priority Data

May 11, 1994 [FI] Finland ..................................... 942196

[51] Int. Cl.[6] ........................ A61M 15/08; A61M 16/00; B05D 7/14; B65D 83/06
[52] U.S. Cl. ................. 128/203.15; 128/203.19; 128/203.23
[58] Field of Search ................. 128/203.15, 203.21, 128/203.19, 203.23

[56] References Cited

U.S. PATENT DOCUMENTS

| | | | |
|---|---|---|---|
| 2,587,215 | 2/1952 | Priestly | 128/203.15 |
| 4,274,403 | 6/1981 | Struve | 128/203.15 |
| 5,113,855 | 5/1992 | Newhouse . | |
| 5,161,524 | 11/1992 | Evans . | |

FOREIGN PATENT DOCUMENTS

| | | |
|---|---|---|
| 2093809 | 2/1993 | Canada . |
| 0079478 | 5/1983 | European Pat. Off. . |
| 0166294 | 1/1986 | European Pat. Off. . |
| 0488609 | 6/1992 | European Pat. Off. . |
| 0546996 | 6/1993 | European Pat. Off. . |
| 2165159 | 4/1986 | United Kingdom . |
| WO90/07351 | 7/1990 | WIPO . |
| WO92/00771 | 1/1992 | WIPO . |
| WO92/09322 | 6/1992 | WIPO . |
| WO92/10229 | 6/1992 | WIPO . |
| WO93/03782 | 3/1993 | WIPO . |
| WO93/16748 | 9/1993 | WIPO . |
| WO94/04210 | 3/1994 | WIPO . |

OTHER PUBLICATIONS

International Search Report dated 24 Jul. 1995.

*Primary Examiner*—Kimberly L. Asher
*Attorney, Agent, or Firm*—Finnegan, Henderson, Farabow, Garrett & Dunner, L.L.P.

[57] ABSTRACT

This device is intended for the dispensing of a powdered medication by inhalation. The device includes a powder container (1), an air channel (2), and a metering strip (4) equipped with a dosing recess (3). The metering strip (4) can be moved along a flat surface (5) from a filling position, in which the dosing recess (3) is filled with powder coming from the container (1), to an inhalation position, in which the dosing recess (3) is in the air channel (2).

12 Claims, 6 Drawing Sheets

POWDER INHALER WITH REMNANT MOVER AND CHAMBER

BACKGROUND OF THE INVENTION

This is a national stage application of International Patent Application No. PCT/FI95/00247.

The invention relates to a device for dispensing of a powdered drug preparation by inhalation. The device is in particular a multiple-dose device without propellant gas, equipped with a metering means which dispenses doses from a powder container. A device such as this is usable, for example, in the treatment of asthma.

The administering of powdered drug preparation by inhalation from an inhaler is commonly known. Multiple-dose type powder inhalers comprising a powder container and a metering member which measures and dispenses a unit dose are also known, for example from patent publications GB 2165159, EP 79478, and EP 166294. In these devices, a series of dosing recesses are notched into the surface of a cylindrical metering member, and the said member is disposed in a chamber of precisely the same shape. When the metering member is rotated, the dosing recesses in turn will move first to a position in alignment with the powder container for being filled and thereafter to a position in alignment with the inhalation channel, whereupon a unit dose will fall by gravity from the dosing recess into the inhalation channel. Thereafter the dose of medication is inhaled from the inhalation channel. These devices have the drawback that they make overdosing of the medication possible by allowing the dispensing of a plurality of doses in succession into the inhalation channel, whereby a multiple dose may be drawn by one inhalation.

Inhalation devices having a metering plate movable between filling and dispensing position are described e.g. in patent publications WO 92/10229, U.S. Pat. No. 5,113,855, U.S. Pat. No. 2587215, EP 546996, WO 94/04210 and U.S. Pat. No. 5161524. However, also these devices suffers from a drawback that they make overdosing possible by allowing the dispensing of a plurality of doses into the inhalation channel.

Attempts have been made to solve this problem by using dispensing systems in which the dosing recess will not be emptied into the inhalation channel by gravity but, instead, the dose of medication is inhaled directly from the dosing recess, such recesses having been notched into the surface of a metering member having the shape of a cylinder, a cone or a truncated cone, as disclosed in patent publications Wo 92/00771 and WO 92/09322. Also in these devices, a metering member having the shape of a cylinder, a cone or a truncated cone is disposed in a chamber having precisely the same shape. When the metering member is rotated, the dosing recesses will move first to a position in alignment with the flow container for filling, and then to the inhalation channel, which is shaped so that the dosing recess will be emptied under the effect of the air flow being inhaled, and thereafter, having rotated through a full 360°, back to a position in alignment with the flow container. The lower surface of the chamber wall may also have an emptying aperture from which any powdered medication possibly left in the dosing recess will fall out during the said rotation.

In the rotating dispensing devices described above, the distance from the filling position to the inhalation position is less than 90° of a circle arc. Since the metering member is, for purposes of metering precision, disposed within a chamber of the same shape, and since it has to be rotated through 360°, of which at least 270° are useless for the actual function of the inhaler, in these devises particles will inevitably fall onto the slide surface between the metering member and the chamber. Thereby the rotation of the highly sensitive metering member will be disturbed and may even be completely obstructed. The metering member jamming in the chamber will hinder the functioning of the whole device. Vigorous shaking or tapping will only increase the jamming, as more powder flows into the gap between the chamber and the metering member.

SUMMARY OF THE INVENTION

The invention relates to a powder inhaler which has the following properties:

1) it can be operated with one hand;
2) the dosage may be easily set for different powder quantities;
3) the device will dispense only one dose at a time;
4) the surfaces rubbing against each other are small, whereby the risk of their jamming is reduced;
5) the track of movement on which the surfaces will rub against each other is small;
6) if desired, any remnants of powder left on the rubbing surfaces and in the inhalation channel can be removed automatically by gravity, without any further steps to be taken or tracks of movement.

The principle of the device according to the invention is illustrated below by way of example, with reference to FIGS. 1–4.

DETAILED DESCRIPTION OF THE INVENTION

Figure 1:
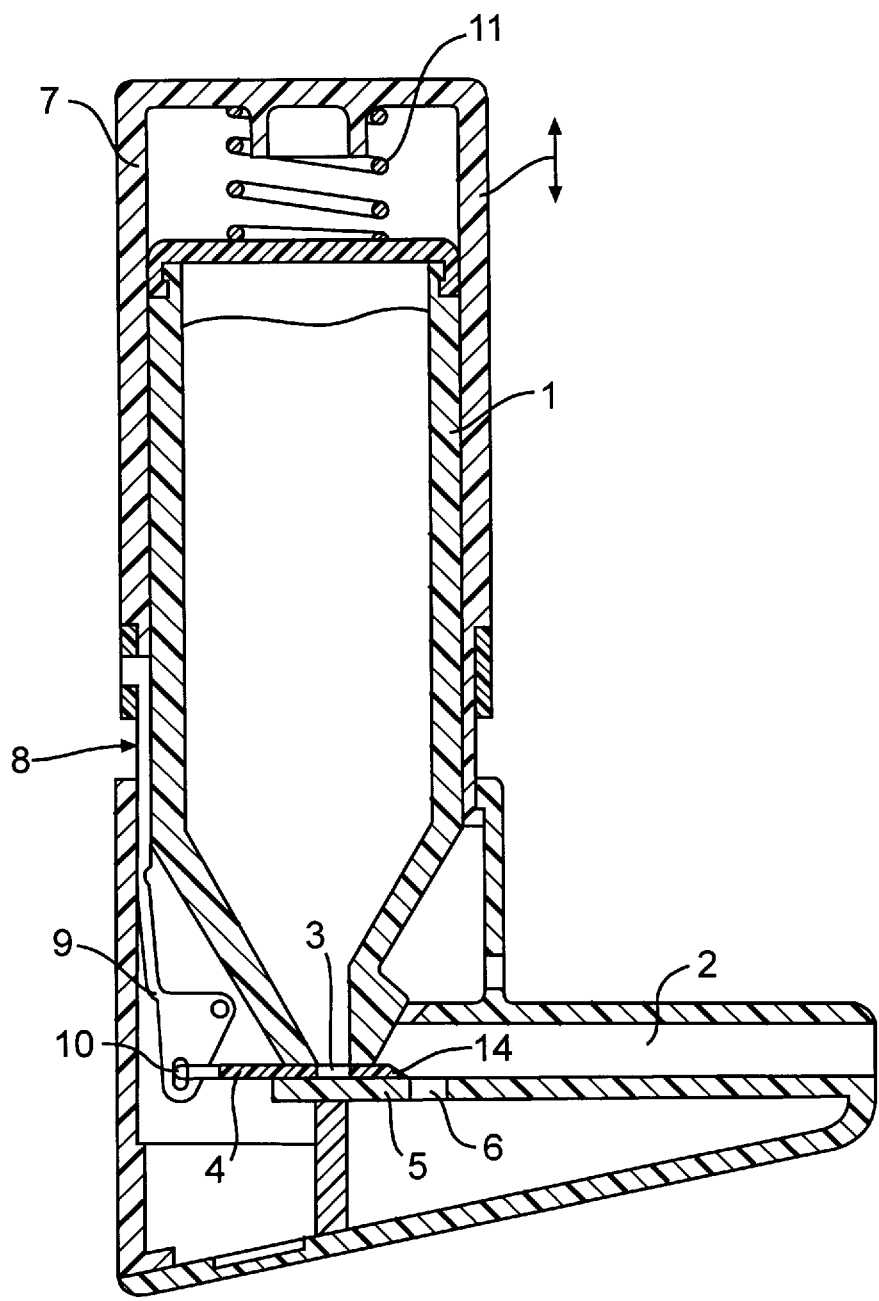
FIG. 1 is a longitudinal view of an embodiment wherein the metering recess (3) is shifted from the filling position to the inhalation position by depression of the outer casing and wherein the dosing recess extends through the metering strip.
Figure 2:
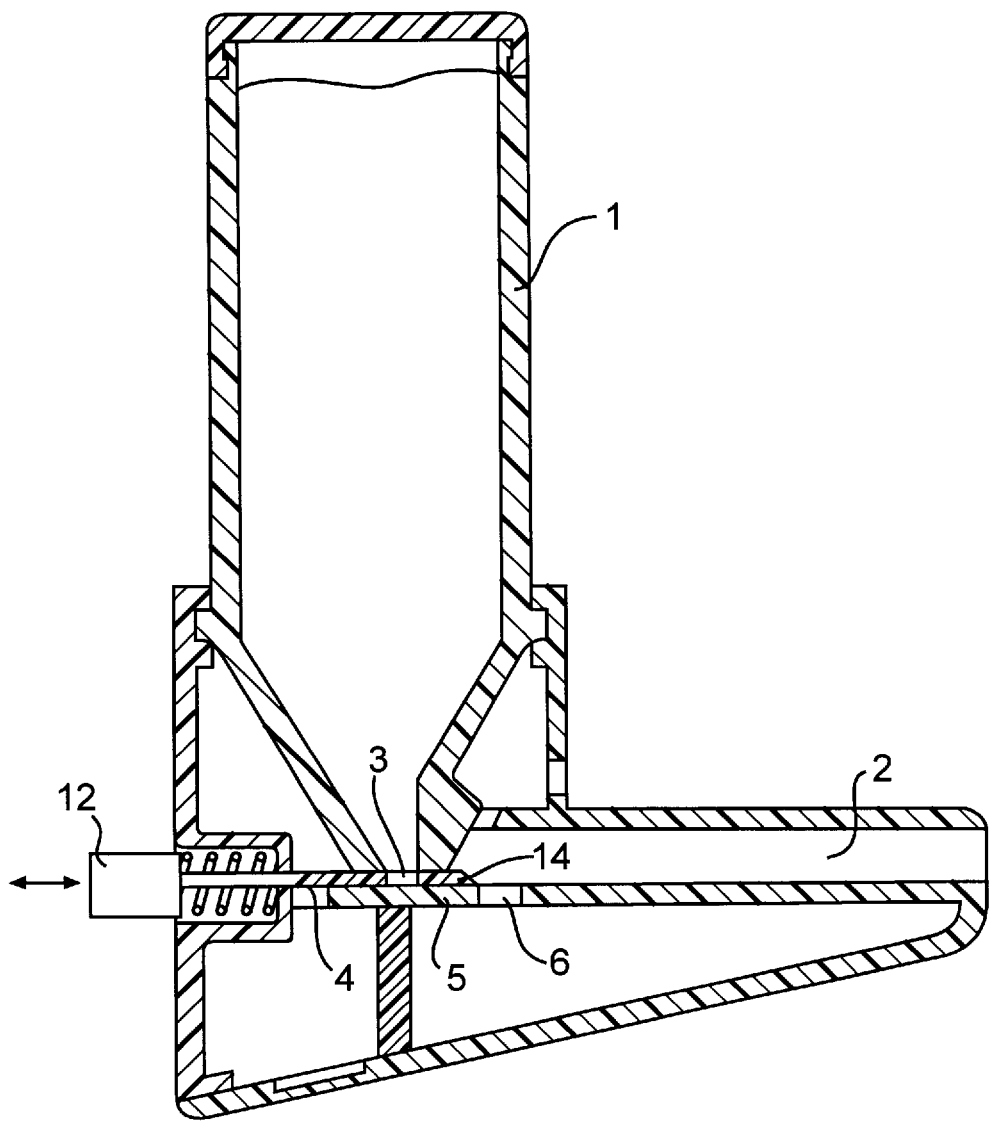
FIG. 2 is a longitudinal view of an embodiment wherein a depression of a button (12) in the back wall of the inhaler will move the metering strip (4) to the inhalation position and wherein the dosing recess extends through the metering strip.
Figure 3:
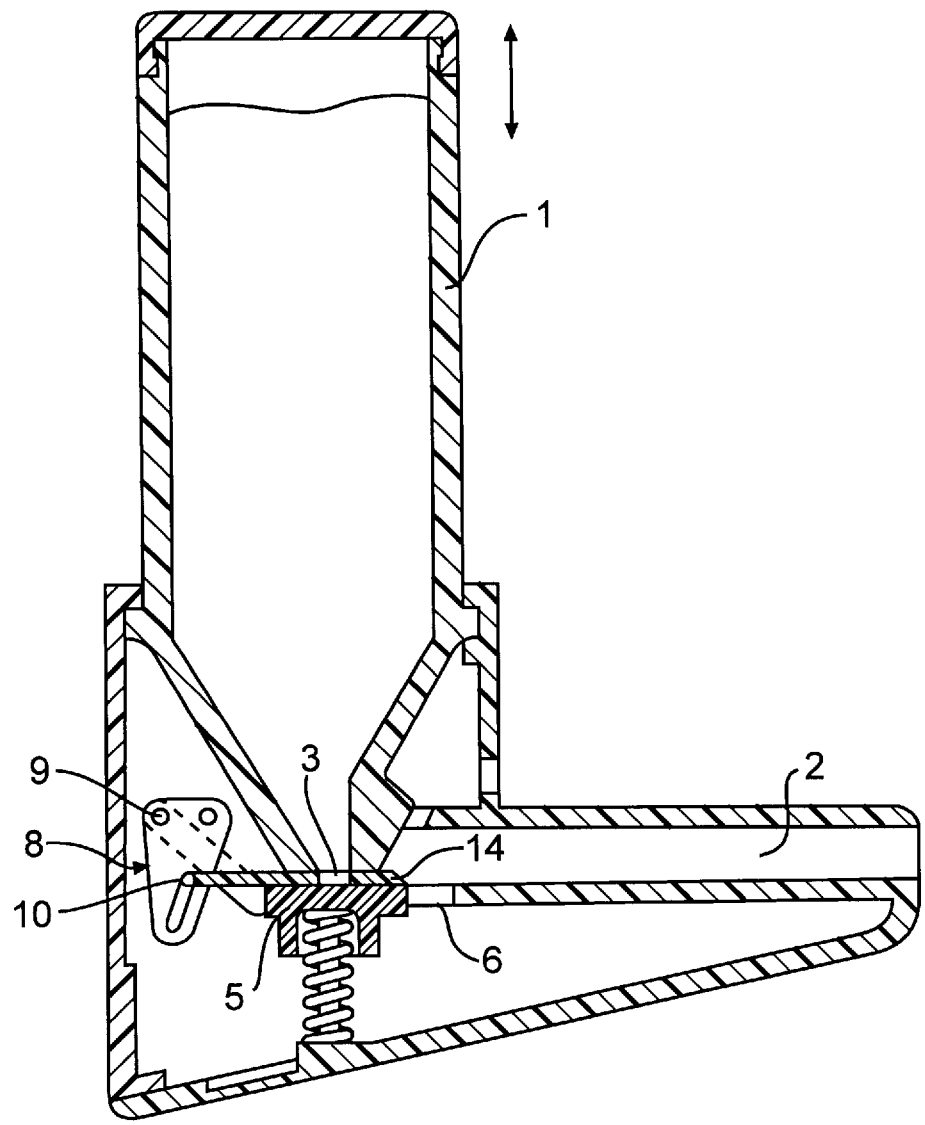
FIG. 3 is a longitudinal view of an embodiment which is a refill inhaler which is operated in the manner of an aerosol container by depressing from the top and wherein the dosing recess extends through the metering strip.
Figure 4:
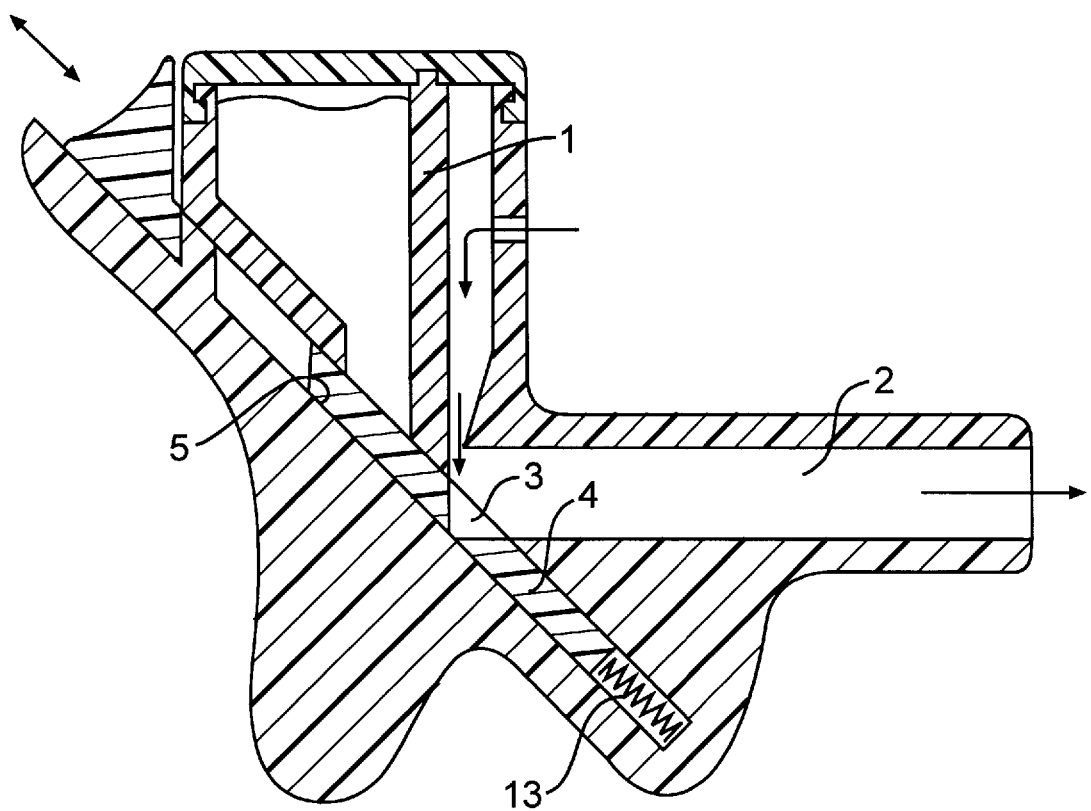
FIG. 4 is a longitudinal view of an embodiment wherein the metering strip (4) and the flat surface (5) are downwardly inclined and wherein the dosing recess extends through the metering strip.
Figure 5:
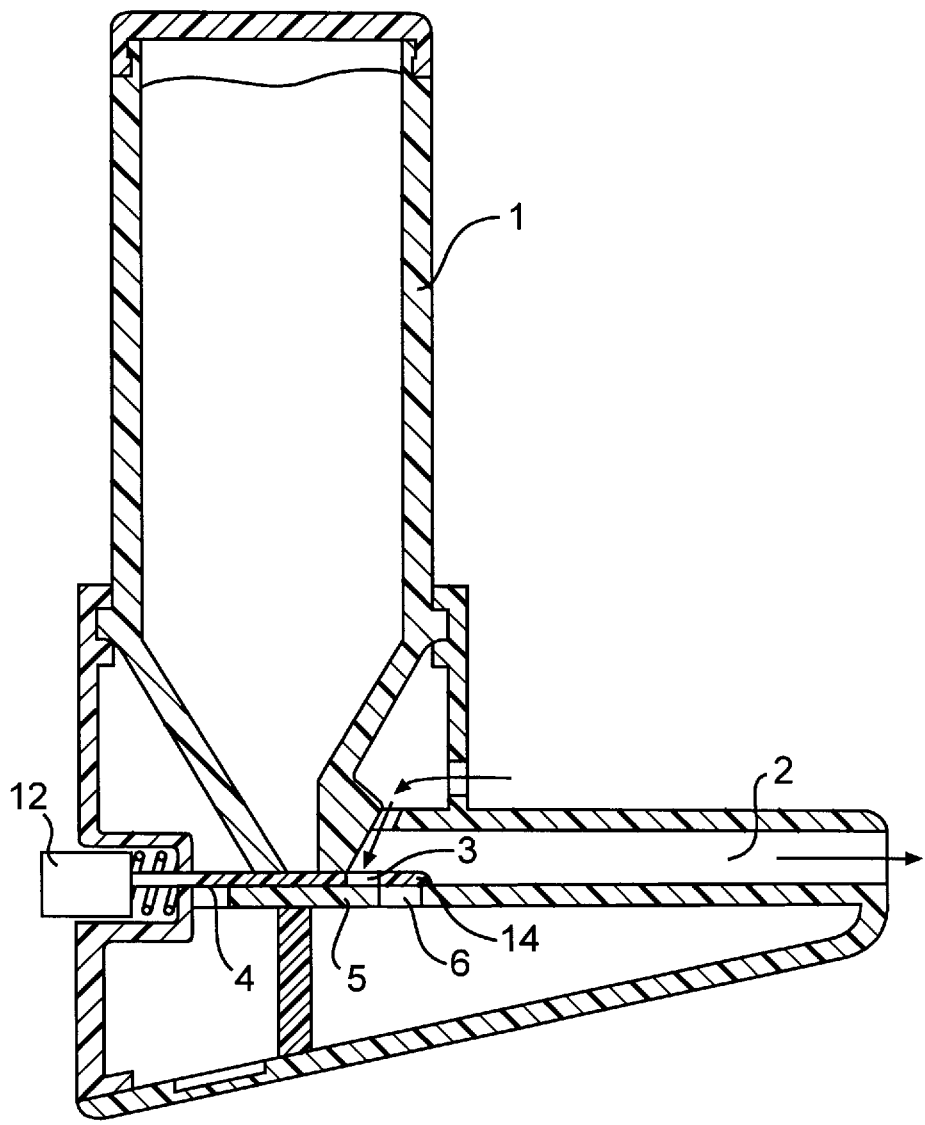
FIG. 5 is a longitudinal view of the embodiment of FIG. 2, wherein the metering strip (4) has moved to the inhalation position by a depression of the button (12) in the back wall of the inhaler.
Figure 6:
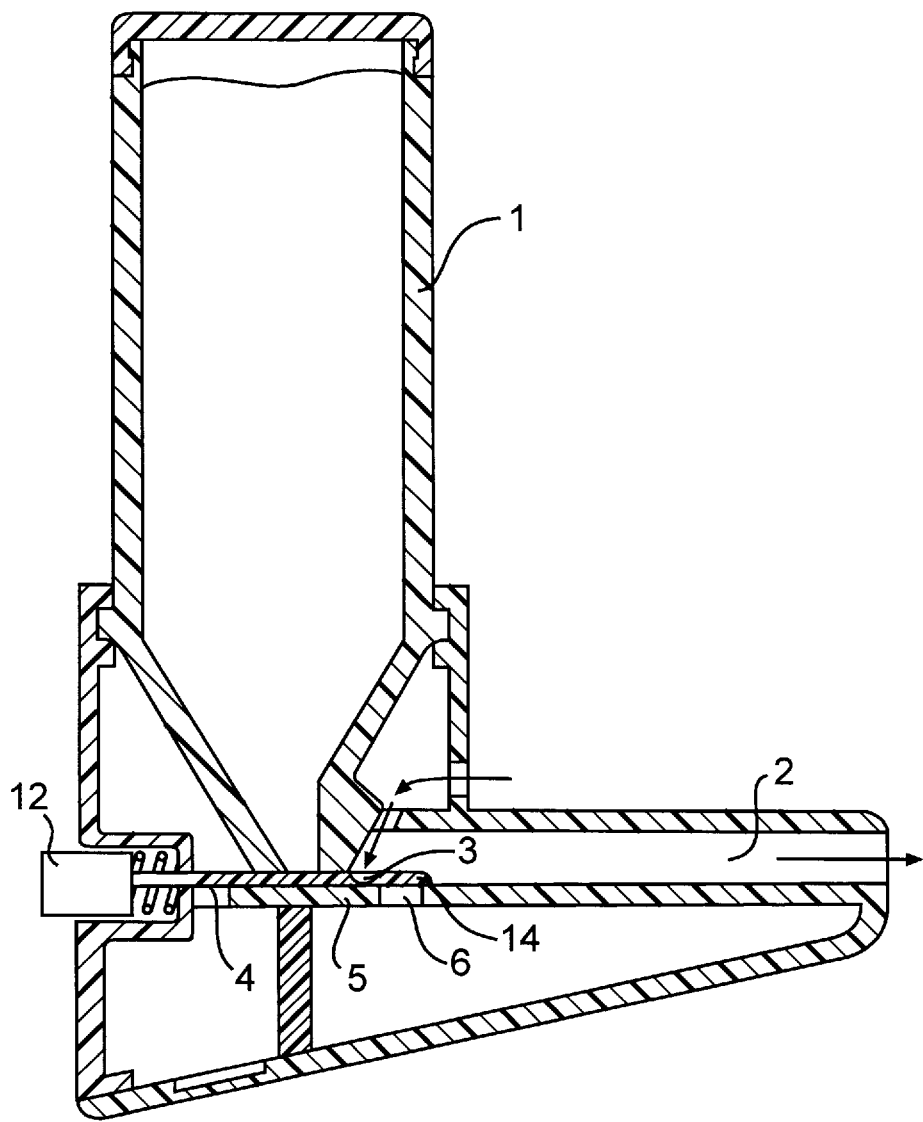
FIG. 6 is a longitudinal view of an embodiment of FIG. 5, wherein the dosing recess (3) has a bottom instead of extending through the metering strip (4).

The powder inhaler according to the invention includes a powder container (1), an air channel (2) through which air is drawn via a mouthpiece, and a metering strip (4) that has a leading edge (14) and is equipped with a dosing recess (3), the strip being disposed on a flat surface (5) and being movable in its longitudinal direction along the flat surface between a first position, in which the dosing recess is filled with powder coming from the container, and a second position, in which the filled dosing recess is brought into the air channel, wherein while the metering strip is in a second position the powder is maintained in the recess by the support of the recess bottom before the inhalation and the air channel is adapted to introduce the air flow into the bottom, as depicted in FIG. 6 of the dosing recess during inhalation whereby the powder is released directly from the dosing recess. In the metering strip the metering recess preferably extends through the metering strip, in which case, in an inhaler ready for use the said flat surface constitutes the bottom of the metering recess, as depicted in FIG 2. Such a metering recess may, for example, simply be drilled through the metering strip.

For the removal of any powder possibly left between the surfaces rubbing against each other, the inhaler may additionally have an aperture for remnants. The aperture for remnants may be constructed so that, when moving along the flat surface between the first and the second positions, the leading edge (14) of the metering strip will travel over the aperture (6) for remnants, at which time any powder possibly remaining between the metering strip and the flat surface will, in normal use of the device, automatically fall via the aperture for remnants as shown in FIGS. 5 and 6 into a chamber for remnants.

The movement of the metering strip between the first and the second positions can be implemented in a number of ways. FIG. 1 depicts an embodiment in which there is, locked to a moving outer casing (7), a lever member (8) which is attached eccentrically to the body and in which articulations (9) and (10) can be effected, for example, by thinning the elastic plastic in the area of the articulation. The metering strip (4) and the lever member may, when so desired, be made as one integral piece. The figure shows how the metering recess is shifted from the filling position to the inhalation position by a depression of the outer casing. When the depressing of the outer casing is discontinued, a return spring (11) will return the casing and the whole mechanism to the initial position. The return spring may be disposed as shown in the figure, or it may be disposed directly in connection with the lever member.

The moving of the metering strip between the two positions may also be implemented in the manner depicted in FIG. 2. This mechanism is straight and simple. By a depression of a button (12) in the back wall of the inhaler, the metering strip (4) will be moved to the inhalation position, as depicted in FIG. 5. In this case the depressible outer casing is unnecessary, and the powder container (1) may as a construction be detachable from the body of the device. In such a refill embodiment the powder container may be attachable to the body, for example, by a snap-fit or by means of threading. The inhaler is thus composed of a body and a powder container attachable thereto. A filled powder container closed with a cap may thus be an independent sales item, which the user can himself connect to the body part. In this case the size of the powder container can be varied widely. Furthermore, problems of shelf life will be reduced, since the combining of the powder container and the metering part will take place only in connection with the device being taken into use.

In the figures referred to above, the flat surface has been depicted as being horizontal when the device is in the normal position for use. It is, however, to be noted that the flat surface (5) need not necessarily be horizontal; the flat surface may also be constructed, for example, so as to be downwardly inclined, in which case also the metering sheet will move slantedly downwards in the normal position for use. This will facilitate the removal of powder from between the flat surface (5) and the metering strip (4).

Many users are accustomed to using conventional aerosol inhalers, which are actuated by depressing from the top. The best aspects of the embodiments depicted in FIGS. 1 and 2 can be combined, whereby a refill inhaler is obtained which is operated in the manner of an aerosol by depressing from the top. Such an embodiment is depicted in FIG. 3. There is no depressible outer casing but, instead, an attachable powder container (1) which is depressed like an aerosol container. The flat surface (5) is constructed so that it is not fixed but, for example, spring-actuated. A depression of the container will cause the lever member (8) to move the metering sheet (4) to the inhalation position. On the other hand, the inhaler of FIG. 2 can be modified so as to have an outer casing, in which case the outer surface of the push button is bevelled so that, when depressed, the outer casing will cover the push button and push it in. In this case the outer casing must have its own return spring.

FIG. 4 depicts an example of an inhaler according to the invention, in which the metering strip (4) and the flat surface (5) are downwardly inclined. This simple inhaler is assembled by snap-fitting the upper and lower pieces together, for example, by means of a snap tabs, after the spring (13) and the metering strip (4) have been placed in their slot. The inhaler may be disposable, in which case the container (1) is filled at the factory and is closed with a cap from above. The inhaler may also be of the refill type, in which case, for example, a drug containing cylinder having a bottom is installed in the powder container while the device is upside down. In this case the inhaler cap can thus be repeatedly opened and closed. The powder container of the inhaler may, of course, also consist of only the said drug-containing cylinder, which is in this case attached to the body of the inhaler by means of, for example, threading.

I claim:

1. A powder inhaler, comprising a powder container (1), an air channel (2) through which air is drawn via a mouthpiece, and a metering strip (4) that has a leading edge (14) and is equipped with a dosing recess (3), wherein said dosing recess (3) has a bottom, and wherein said metering strip (4) is disposed on a flat surface (5) and is movable in its longitudinal direction along said flat surface (5) between a first position in which said dosing recess (3) is filled with a powder coming from said container (1), and a second position in which said filled dosing recess (3) is brought into said air channel (2), wherein the powder is maintained in said dosing recess (3) by the support of said bottom, and wherein said air channel (2) is directed to introduce an air flow into said dosing recess (3) during inhalation whereby the powder is released directly from said dosing recess (3), and an aperture (6) for remnants, wherein said leading edge (14) of said metering strip (4) travels towards and over said aperture (6) for remnants when said metering strip (4) moves between the filling and the inhalation positions, at which time any powder remaining between said leading edge (14) of said metering strip (4) and said flat surface (5) is moved by said leading edge (14) to fall through said aperture (6) for remnants.

2. The inhaler according to claim 1, wherein said inhaler has a return mechanism which will automatically return said metering strip (4) from the inhalation position to the filling position.

3. The inhaler according to claim 2, wherein said inhaler has a depressible outer casing (7) and a lever member (8) locked thereto.

4. The inhaler according to claim 1, wherein said inhaler has a depressible outer casing (7) and a lever member (8) locked thereto.

5. The inhaler according to any one of claims 1–4, wherein said powder container (1) is detachable from said inhaler.

6. The inhaler according to claim 5, wherein said powder container (1) is depressible.

7. A powder inhaler, comprising a powder container (1), an air channel (2) through which air is drawn via a mouthpiece, and a metering strip (4) that has a leading edge (14) and is equipped with a dosing recess (3), wherein said dosing recess (3) extends through said metering strip (4), and wherein said metering strip (4) is disposed on a flat surface (5) and is movable in its longitudinal direction along said flat surface (5) between a first position in which said dosing recess (3) is filled with a powder coming from said container (1), and a second position in which said filled dosing recess (3) is brought into said air channel (2), wherein the powder is maintained in said dosing recess (3) by the support of said flat surface (5) which constitutes a bottom of said dosing recess (3), and wherein said air channel (2) is directed to introduce an air flow into said dosing recess (3) during inhalation whereby the powder is released directly from said dosing recess (3), and an aperture (6) for remnants, wherein said leading edge (14) of said metering strip (4) travels towards and over said aperture (6) for remnants when said metering strip (4) moves between the filling and the inhalation positions, at which time any powder remaining between said leading edge (14) of said metering strip (4) and said flat surface Is moved by said leading edge (14) to fall through said aperture (6) for remnants.

8. The inhaler according to claim 7, wherein said inhaler has a return mechanism which will automatically return the metering strip (4) from the inhalation position to the filling position.

9. The inhaler according to claim 8, wherein said inhaler has a depressible outer casing (7) and a lever member (8) locked thereto.

10. The inhaler according to claim 7, wherein said inhaler has a depressible outer casing (7) and a lever member (8) locked thereto.

11. The inhaler according to any one of claims 7–10, wherein said powder container (1) is detachable from said inhaler.

12. The inhaler according to claim 11, wherein said powder container (1) is depressible.

* * * * *